United States Patent [19]

Pretzer et al.

[11] 4,239,705

[45] Dec. 16, 1980

[54] PROCESS FOR PRODUCING ACETALDEHYDE

[75] Inventors: Wayne R. Pretzer; Thaddeus P. Kobylinski, both of Gibsonia; John E. Bozik, Pittsburgh, all of Pa.

[73] Assignee: Gulf Research & Development Company, Pittsburgh, Pa.

[21] Appl. No.: 42,427

[22] Filed: May 25, 1979

Related U.S. Application Data

[63] Continuation-in-part of Ser. No. 936,718, Aug. 25, 1978, abandoned.

[51] Int. Cl.$^3$ ............................................. C07C 47/06
[52] U.S. Cl. ................................................... 568/487
[58] Field of Search ..... 260/601 R, 604 HF, 604 AC, 260/603 R

[56] References Cited

U.S. PATENT DOCUMENTS

| | | | |
|---|---|---|---|
| 3,356,764 | 12/1967 | Kuraishi et al. | 260/601 R |
| 3,576,734 | 4/1971 | Senn | 260/604 HF |
| 3,627,843 | 12/1971 | Pregaglia et al. | 260/604 HF |
| 3,996,288 | 12/1976 | Yukata et al. | 260/604 HF |
| 4,151,208 | 4/1979 | Pretzer et al. | 260/601 R |

*Primary Examiner*—Werren B. Lone

[57] ABSTRACT

A process for selectively producing acetaldehyde which comprises introducing into a reaction zone (1) methanol, (2) hydrogen, (3) carbon monoxide, (4) an arsenic-cobalt tricarbonyl complex and (5) an iodine compound and then subjecting the contents of said reaction zone to an elevated temperature and an elevated pressure for a time sufficient to convert methanol to acetaldehyde.

12 Claims, No Drawings

PROCESS FOR PRODUCING ACETALDEHYDE

This application is a continuation-in-part application of our U.S. Pat. application Ser. No. 936,718, filed Aug. 25, 1978, now abandoned for A PROCESS FOR PRODUCTION OF ACETALDEHYDE FROM METHANOL, CARBON MONOXIDE AND HYDROGEN USING AN ARSENIC-COBALT TRICARBONYL COMPLEX AND AN IODINE PROMOTER.

BACKGROUND OF THE INVENTION

1. Field of the Invention

This invention is directed to a process for selectively producing acetaldehyde which comprises introducing into a reaction zone (1) methanol, (2) hydrogen, (3) carbon monoxide, (4) an arsenic-cobalt tricarbonyl complex, and (5) an iodine compound and then subjecting the contents of said reaction zone to an elevated temperature and an elevated pressure for a time sufficient to convert methanol to acetaldehyde.

2. Description of the Prior Art

The synthesis of oxygenated hydrocarbons, such as aldehydes, alcohols, etc., by reacting methanol with synthesis gas (hydrogen and carbon monoxide) is not a new concept. Processes are available for producing a wide spectrum of oxygen-containing hydrocarbons, such as alcohols, aldehydes, ketones, esters, ethers and fatty acids of almost any chain length and degree of saturation. The relative amount or extent to which one or more of the above-described products is obtained is determined and/or controlled by the type catalyst used in the reaction. Catalysts which have been used in the past to produce aldehydes, alcohols, etc., are those selected from iron, cobalt, nickel, zinc and the like on a support, either alone or in combination with one or more promoter(s).

The conversion of an alcohol, for example, methanol, to an aldehyde, such as acetaldehyde, containing one carbon atom more than the original alcohol is normally a tedious and time-consuming procedure involving a series of steps. Additionally, catalysts which possess acceptable activity generally tend to give a wide spectrum of products, for example, hydrocarbons and oxygenated hydrocarbons having a broad distribution of carbon atoms. This not only complicates the separation and recovery of desired products, but results in reduced yield of said desired products and erosion of reactants in the production of undesirable products. The process herein is particularly suited to the selective formation of acetaldehyde from methanol and synthesis gas using an arsenic-cobalt tricarbonyl complex in combination with an iodine promoter.

The reaction of methanol with hydrogen and carbon monoxide to produce acetaldehyde is appreciated and disclosed by the prior art. However, most known processes produce an undesirably large mixture of alcohols, ketones and carboxylic acids in addition to the desired aldehyde.

U.S. Pat. No. 3,356,734, issued to Kurahhi et al, on Dec. 5, 1967, entitled "Process for the Production of Acetaldehyde", teaches a process for the production of acetaldehyde in two steps. In the first step, methanol, hydrogen and carbon monoxide are contacted with a cobalt catalyst and a halogen promoter to form a product predominating in acetals. The cobalt catalyst described is selected from cobalt salts which are soluble in methanol. In particular, preferred soluble salts include cobalt acetate, cobalt bromide, chlorate, chloride, iodide, sulfide and the like. The halogen promoter is selected from iodine, bromine, chlorine and the like. In the second step, the acetals so produced are contacted with a second distinct catalyst system to hydrolyze the acetals to acetaldehyde and methanol. Maximum possible selectivity to acetaldehyde is from about 17 to about 38 mol percent of the converted methanol.

Another process for producing aldehydes is disclosed in U.S. Pat. No. 3,996,288, entitled "Method of Producing Aldehydes by Hydroformylation"; issued to Yukata et al, on Dec. 7, 1976. Particularly, the reference relates to a process for preparing phenylacetaldehyde by contacting hydrogen, carbon monoxide, an amide of a carboxylic acid and benzyl chloride at elevated temperature and pressure in the presence of a carbonylation catalyst, for example, dicobalt octacarbonyl. The reference, however, fails to appreciate a process for the selective formation of acetaldehyde from methanol, hydrogen and carbon monoxide.

SUMMARY OF THE INVENTION

The present invention relates to a process for selectively producing acetaldehyde which comprises introducing into a reaction zone (1) methanol, (2) hydrogen, (3) carbon monoxide, (4) an arsenic-cobalt tricarbonyl complex, and (5) and iodine compound and then subjecting the contents of said reaction zone to an elevated temperature and an elevated pressure for a time sufficient to convert methanol to acetaldehyde.

From the above it can be seen that for the purposes of the process defined and claimed herein five separate and distinct entities are introduced into a reaction zone prior to subjecting them to an elevated temperature and elevated pressure sufficient to obtain acetaldehyde. Of these the arsenic-cobalt tricarbonyl complex and the iodine entity require further elucidation.

The arsenic-cobalt tricarbonyl complex used herein can be defined by the following formula:

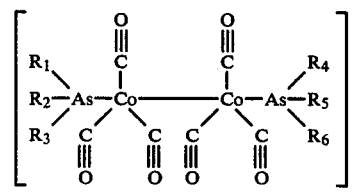

wherein $R_1$, $R_2$, $R_3$, $R_4$, $R_5$ and $R_6$ are either alike or different members selected from the group consisting of alkyl radicals having from one to 24 carbon atoms, preferably from two to 10 carbon atoms; aryl radicals having from six to 20 carbon atoms, preferably from six to 10 carbon atoms; alkenyl radicals having from two to 30 carbon atoms, preferably from two to 20 carbon atoms; cycloaklyl radicals having from three to 40 carbon atoms, preferably from three to 30 carbon atoms and aralkyl and alkaryl radicals having from six to 40 carbon atoms, preferably from six to 30 carbon atoms; with the requirement that at least one R must be aryl, aralkyl or alkaryl.

Arsenic-cobalt tricarbonyl complexes which are suitable for use herein include:
methyl diphenyl arsine cobalt tricarbonyl dimer
dimethyl phenyl arsine cobalt tricarbonyl dimer
triphenyl arsine cobalt tricarbonyl dimer
tri-p-tolyl arsine cobalt tricarbonyl dimer cyclohexyl diphenyl arsine cobalt tricarbonyl dimer
trinaphthyl arsine cobalt tricarbonyl dimer
vinyl diphenyl arsine cobalt tricarbonyl dimer
styryl diphenyl arsine cobalt tricarbonyl dimer, or
benzyl (p-tolyl) arsine cobalt tricarbonyl dimer,
and mixtures thereof.

Any source of iodine which is capable of disassociating, that is, ionizing to form free iodide ions in the reaction medium, can be used in the present invention. Illustrative examples of iodine compounds especially suitable for use herein include iodine, potassium iodide, calcium iodide, sodium iodide, lithium iodide, hydrogen iodide, methyl iodide, ethyl iodide, etc.

The relative amounts of carbon monoxide and hydrogen employed can be varied over a wide range. However, in general, the molar ratio range of carbon monoxide to hydrogen is from about 1:10 to about 10:1, especially from about 1:3 to about 3:1; however, conventional synthesis gas (mixtures of carbon monoxide and hydrogen) with a molar ratio of about 1:1 is convenient and satisfactory for the process herein. It is to be noted that molar ratios outside the aforestated ratio ranges can be employed herein. Compounds or reaction mixtures which give rise to the formation of carbon monoxide and hydrogen under the reaction conditions defined herein can be used instead of mixtures comprising carbon monoxide and hydrogen which are used in the preferred embodiments of this invention.

The arsenic-cobalt tricarbonyl complex and the iodine entity are introduced into the reaction zone in molar ratios, based on the elements cobalt and iodine, respectively, ranging from about 100:1 to about 1:100, preferably about 20:1 to about 1:20. Based on the methanol introduced into the system, the weight percent of combined cobalt and iodine, in their elemental form, can range from about 0.01 to about 10 percent, preferable from about 0.1 to about five percent.

The process defined herein can be carried out either in a batch operation or by passing the reactants continuously through a reaction zone. In each case the reactor is provided with agitation means and the pressure is maintained therein by the addition of hydrogen and carbon monoxide as required. In order to facilitate introduction of the arsenic-cobalt tricarbonyl complex and the iodine entity into the reaction zone and/or to facilitate recovery of the components of the reaction herein, they can be dissolved in an inert solvent such as ethylene glycol, diethylene glycol monomethyl ether, acetone, etc.

In the reaction zone the contents thereof are maintained at an elevated temperature and an elevated pressure for a time sufficient to convert methanol to acetaldehyde. Pressures which are suitable for use herein generally are above about 1000 pounds per square inch gauge (6.83 MPa), but should not be in excess of about 10,000 pounds per square inch gauge (68.30 MPa). An especially desirable pressure range is from about 1000 pounds per square inch gauge (6.83 MPa) to about 6000 pounds per square inch gauge (40.98 MPa), preferably from about 2000 pounds per square inch gauge (13.66 MPa) to about 5000 pounds per square inch gauge (34.15 MPa). Temperatures which are suitable for use herein are those temperatures which initiate a reaction between the reactants herein to selectively produce acetaldehyde, generally from about 150° C. to about 250° C., preferably from about 175° C. to about 225° C. The reaction is conducted for a time period sufficient to convert methanol to acetaldehyde, normally from about 0.5 hour to about 10 hours, especially from about one to about five hours.

Recovery of the desired acetaldehyde from the reaction product can be effected in any convenient or conventional manner, for example, by distillation. At ambient pressure and about 21° C., the components will distill off in the following sequence for the desired recovery: dimethyl ether, acetaldehyde, methyl acetate, methanol and ethanol.

It is to be noted that the catalyst system herein is highly selective to the formation of acetaldehyde and minimizes the formation of undesirable by-products such as alcohols, ethers, esters and other alcohol derivatives.

DESCRIPTION OF PREFERRED EMBODIMENTS

The following Examples and Tables serve to further illustrate and instruct one skilled in the art the best mode of how to practice this invention and are not intended to be construed as limiting thereof.

The reactions herein were performed in a stainless steel pressure-resistant autoclave equipped with agitation means, for example, a type 316 stainless steel, 300 cc. autoclave marketed commercially by Autoclave Engineers. The methanol, hydrogen, carbon monoxide, arsenic-cobalt tricarbonyl complex and iodine promoter were introduced into the autoclave. The autoclave was connected to another larger reservoir containing synthesis gas (hydrogen and carbon monoxide) which fed said synthesis gas into the steel autoclave at a set pressure on demand. Thus, the reactor pressure was maintained throughout the course of the reaction. The reaction pressure and temperature were adjusted to operating conditions and the mixture reacted for a period of time sufficient to produce acetaldehyde.

EXAMPLES I-III

Into a 300 cc. stainless steel autoclave were charged three millimoles of the defined arsenic-cobalt tricarbonyl complex, 0.75 millimole of iodine and 100 milliliters of methanol (see Table I). The reactor was next purged twice with nitrogen gas and then pressurized with synthesis gas ($H_2:CO=1$) to a pressure of about 1000 pounds per square inch gauge (6.83 MPa) lower than the desired working pressure. The system was then heated to a temperature of about 200° C., and the pressure was adjusted to a working pressure of about 4000 pounds per square inch gauge (27.6 MPa). The reaction was allowed to proceed for approximately three hours, after which the reactor was cooled by an internal cooling coil to about −75° C. The reactor was vented through a dry gas meter and a gas sample was taken for a mass spectral analysis, and the liquid product was analyzed using a Model 900 Perkin-Elmer gas chromatograph utilizing a 16 ft. (4.88 meters)×1.8 in. (0.32 centimeter) stainless steel column wherein eight ft. (2.44 meters) of the column was packed with 80/100 mesh Poropak Q and the other eight ft. (2.44 meters) was packed with 80/100 mesh Poropak R. Poropak Q and Poropak R are polyvinyl benzene type resins which are marketed commercially by Waters Associates, a corporation located in Milford, Mass. The gas chromatograph was programmed to increase from 40° C. to 190° C. at a rate of 32° C./min. and with a helium flow rate of 30 cc./min. The above procedure was followed in the Examples set forth in Table I below.

TABLE I

| Example No. | Catalyst System | Percent MeOH[a] Conv. | Mole Percent Selectivity | | | | |
|---|---|---|---|---|---|---|---|
| | | | $Me_2O^b$ | $AcH^c$ | $EtOH^d$ | $MeOAc^e$ | $Other^f$ |
| I | Tri-phenyl arsine cobalt tricarbonyl dimer + iodine | 70.8 | 6.7 | 52.9 | 18.1 | 12.7 | 9.6 |
| II | Tri-p-tolyl arsine cobalt tricarbonyl dimer | 41.2 | 5.8 | 55.5 | 15.0 | 10.4 | 13.3 |
| III | Methyl diphenyl arsine cobalt tricarbonyl dimer | 39.1 | 5.0 | 51.8 | 22.1 | 10.4 | 10.7 |

[a] MeOH = Methanol
[b] $Me_2O$ = Dimethyl ether
[c] AcH = Acetaldehyde
[d] EtOH = Ethanol
[e] McOAc = Methyl acetate
[f] Other = Mixtures of ethyl acetate, methyl formate, propanols, propionaldehyde, butanols, n-butyraldehyde and methane As can readily be seen from the above data, the catalyst system herein is selective to acetaldehyde formation under the specified reaction conditions.

EXAMPLES IV and V

The procedure of Examples I to III was followed with the following exceptions; in Example IV, phosphorus was substituted for the arsenic in the cobalt complex; in Example V, antimony was substituted for the arsenic in the cobalt complex. The results are tabulated in Table II below.

TABLE II

| Example No. | Catalyst System | Percent MeOH[a] Conv. | Mole Percent Selectivity | | | | | |
|---|---|---|---|---|---|---|---|---|
| | | | $Me_2O^b$ | $AcH^c$ | $EtOH^d$ | $MeOAc^e$ | $Et_2O^f$ | $Other^g$ |
| IV | Tri-phenyl phosphine-cobalt tricarbonyl dimer + iodine | 60.3 | 4.0 | 13.6 | 60.3 | 13.8 | 8.3 | None |
| V | Tri-phenyl antimony-cobalt tricarbonyl dimer + iodine | 66.4 | 9.7 | 28.8 | 31.9 | 18.3 | None | 11.3 |

[a] MeOH = Methanol
[b] $Me_2O$ = Dimethyl ether
[c] AcH = Acetaldehyde
[d] EtOH = Ethanol
[e] MeOAc = Methyl acetate
[f] $Et_2O$ = Diethyl ether
[g] Other = Mixtures of ethyl acetate, methyl formate, propanols, propionaldehyde, butanols, n-butyraldehyde and methane A comparison of the data in Table II with that of Table I show the criticality of using the specified arsenic-cobalt tricarbonyl complex herein. When tri-phenyl phosphine-cobalt tricarbonyl dimer and tri-phenyl antimony-cobalt tricarbonyl dimer were used in place of one of the specified arsenic-cobalt tricarbonyl complexes, selectivity to acetaldehyde was greatly reduced but selectivity to ethanol was greatly increased.

Obviously, many modifications and variations of the invention, as hereinabove set forth, can be made without departing from the spirit and scope thereof, and therefore only such limitations should be imposed as are indicated in the appended claims.

We claim:

1. A process for selectively producing acetaldehyde which comprises introducing into a reaction zone (1) methanol, (2) hydrogen, (3) carbon monoxide, (4) an arsenic-cobalt tricarbonyl complex defined by the following formula:

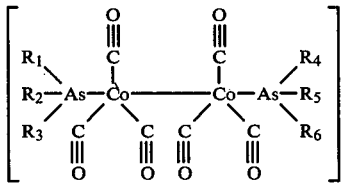

wherein $R_1$, $R_2$, $R_3$, $R_4$, $R_5$ and $R_6$ are members selected from the group consisting of phenyl and alkyl substituted phenyl and (5) an iodine compound, the arsenic-cobalt tricarbonyl complex and the iodine entity being present in a molar ratio of about 100:1 to about 1:100, the weight percent of combined cobalt tricarbonyl complex and the iodine entity, as elements, being present in the range of about 0.01 to about 10 percent, the molar ratio of carbon monoxide to hydrogen being about 1:10 to about 10:1, and then subjecting the contents of said reaction zone to an elevated temperature of about 150° to about 250° C. and an elevated pressure of about 1000 to about 6000 pounds per square inch gauge for a time within the range of about 0.5 to about 10 hours sufficient to convert methanol to acetaldehyde.

2. The process of claim 1 wherein the arsenic-cobalt tricarbonyl complex is tri-phenyl arsine cobalt tricarbonyl dimer.

3. The process of claim 1 wherein the arsenic-cobalt tricarbonyl complex is tri-p-tolyl arsine cobalt tricarbonyl dimer.

4. The process of claim 1 wherein the arsenic-cobalt tricarbonyl complex is methyl diphenyl arsine cobalt tricarbonyl dimer.

5. The process of claim 1 wherein the iodine compound is a member selected from the group consisting of iodine, potassium iodide, calcium iodide, sodium iodide, lithium iodide, hydrogen iodide, methyl iodide and ethyl iodide or mixtures thereof.

6. The process of claim 1 wherein the iodine promoter is iodine.

7. The process of claim 1 wherein the arsenic-cobalt tricarbonyl complex and the iodine entity are present in a molar ratio of about 20:1 to about 1:20.

8. The process of claim 1 wherein the weight percent of the combined cobalt tricarbonyl complex and the iodine entity, as elements, is in the range of about 0.1 to about five percent.

9. The process of claim 1 wherein the reaction temperature is about 175° C. to about 225° C.

10. The process of claim 1 wherein the reaction pressure is about 2000 pounds per square inch gauge to about 5000 pounds per square inch gauge.

11. The process of claim 1 wherein the reaction time is about one hour to about five hours.

12. The process of claim 1 wherein the molar ratios of carbon monoxide to hydrogen are about 1:3 to about 3:1.

* * * * *